(12) United States Patent
Holder

(10) Patent No.: US 10,500,541 B2
(45) Date of Patent: Dec. 10, 2019

(54) CHEMICAL ABSORBENT

(71) Applicant: INTERSURGICAL AG, Vaduz (LI)

(72) Inventor: Michael John Holder, Wokingham (GB)

(73) Assignee: Intersurgical AG, Vaduz (LI)

( * ) Notice: Subject to any disclaimer, the term of this patent is extended or adjusted under 35 U.S.C. 154(b) by 0 days.

(21) Appl. No.: 15/520,758

(22) PCT Filed: Oct. 26, 2015

(86) PCT No.: PCT/EP2015/074772
§ 371 (c)(1),
(2) Date: Apr. 20, 2017

(87) PCT Pub. No.: WO2016/066595
PCT Pub. Date: May 6, 2016

(65) Prior Publication Data
US 2017/0320011 A1  Nov. 9, 2017

(30) Foreign Application Priority Data
Oct. 28, 2014 (GB) .................... 1419164.7

(51) Int. Cl.
| | |
|---|---|
| *B01J 20/04* | (2006.01) |
| *B01J 20/18* | (2006.01) |
| *B01J 20/30* | (2006.01) |
| *B01D 53/62* | (2006.01) |
| *A61M 16/22* | (2006.01) |
| *A61M 16/08* | (2006.01) |

(52) U.S. Cl.
CPC ......... *B01D 53/62* (2013.01); *A61M 16/0891* (2014.02); *A61M 16/22* (2013.01); *B01J 20/041* (2013.01); *B01J 20/186* (2013.01); *B01J 20/3007* (2013.01); *B01D 2251/404* (2013.01); *B01D 2251/604* (2013.01); *B01D 2253/108* (2013.01); *B01D 2257/504* (2013.01)

(58) Field of Classification Search
None
See application file for complete search history.

(56) References Cited

U.S. PATENT DOCUMENTS

| | | | |
|---|---|---|---|
| 6,562,748 B2 * | 5/2003 | Holder | B01J 2/22 502/400 |
| 2002/0072466 A1 | 6/2002 | Holder | |
| 2003/0019356 A1 * | 1/2003 | Herden | B01D 53/12 95/108 |
| 2004/0029730 A1 * | 2/2004 | Clarke | B01D 53/62 502/404 |
| 2004/0053782 A1 | 3/2004 | Holder | |

FOREIGN PATENT DOCUMENTS

| | | |
|---|---|---|
| CN | 102489147 A | 6/2012 |
| EP | 1041349 A2 | 10/2000 |
| JP | 86121077 A | 1/1986 |
| JP | 61293546 A | 12/1986 |
| WO | 87/01965 A1 | 4/1987 |
| WO | 98/17385 A1 | 4/1998 |
| WO | 02/16027 A1 | 2/2002 |
| WO | 2002/032493 A1 | 4/2002 |

OTHER PUBLICATIONS

International Preliminary Report on Patentability and the Written Opinion for International Patent Application No. PCT/EP2015/074772 (dated May 11, 2017).
Great Britain Search Report corresponding to GB1419164.7, dated Jun. 3, 2015.
International Search Report and Written Opinion corresponding to PCT/EP2015/074772, dated Feb. 16, 2016.

* cited by examiner

*Primary Examiner* — Daniel Berns
(74) *Attorney, Agent, or Firm* — Pepper Hamilton LLP

(57) ABSTRACT

A chemical absorbent comprising a hydrated mixture of a major proportion of a pharmaceutically acceptable hydroxide of a Group II metal and a minor proportion of a Group I metal-containing zeolite. The chemical absorbent is substantially free of hydroxides of Group I metals.

16 Claims, No Drawings

CHEMICAL ABSORBENT

This application is a national stage application under 35 U.S.C. § 371 of PCT Application No. PCT/EP2015/074772, filed Oct. 26, 2015, which claims the priority benefit of Great Britain Patent Application No. 1419164.7, filed Oct. 28, 2014.

This invention relates to a chemical absorbent, and in particular to an absorbent for carbon dioxide which is useful in low flow or closed circuit anaesthesia.

Chemical absorbents are used to remove one or more molecular species from a medium, for example to remove specific molecular species from mixtures of gases. Soda lime is one such chemical absorbent and is widely used to absorb carbon dioxide, for instance in anaesthetic breathing systems and other applications involving air which is to be breathed.

In order to make chemically active soda lime, calcium hydroxide is mixed with sodium hydroxide and/or potassium hydroxide to produce a highly alkaline lime mixture containing water. The alkaline lime mixture typically contains (on a dry basis) 96-98% by weight calcium hydroxide and 2-4% by weight sodium and/or potassium hydroxide. The finished product typically contains 81-87% w/w alkaline lime mixture and 13-19% w/w water. In addition, a pH sensitive indicator dye is normally present to give a visual indication of the extent of usage and exhaustion. This indicator dye is present in the alkaline lime mixture at very low levels, typically 0.01-0.1% w/w.

The mechanism by which soda lime absorbs carbon dioxide is understood to be as follows:
  (i) carbon dioxide reacts with water to form carbonic acid,
  (ii) an acid-base reaction between the carbonic acid and sodium or potassium hydroxide forms sodium or potassium carbonate and water,
  (iii) ion exchange occurs between the sodium or potassium carbonate and calcium hydroxide to form calcium carbonate and to regenerate sodium or potassium hydroxide.

The sodium or potassium hydroxide level is thus maintained and this acts as a catalyst to accelerate and prolong absorption.

Though first introduced early in the twentieth century, soda lime remains the most widely used carbon dioxide absorbent for use in anaesthesia. However, its use is accompanied by certain disadvantages or concerns.

A major concern in the field of anaesthesia in recent years has been unwanted reactions between volatile anaesthetic agents and the soda lime absorbent. If these interactions occur to a great enough extent, they can lead to low levels of potentially toxic compounds building up in the patient breathing circuit. The levels are very low, but nevertheless there is a growing awareness of the issue and increasing concern amongst anaesthetists. These degradation products are of most concern when the soda lime has been allowed to become excessively dry. This rarely happens in normal use but there are certain practices under which it can occur. Two issues of particular concern are the production of carbon monoxide and a highly exothermic degradation reaction with the widely used anaesthetic agent "Sevoflurane".

Another problem that occurs with soda lime formulations is that dust and fine particles are formed as a result of the friability and breakdown of the product. The presence of such dust is highly undesirable, particularly when the product is intended for use in anaesthetic (or other) breathing systems since the fine particles may be inhaled. International Patent Application WO 98/17385 discloses formulations which address this problem. These formulations contain a small proportion of zeolite which increases the mechanical strength of the soda lime granules. However, these formulations also contain conventional proportions of sodium and/or potassium hydroxide.

International Patent Application WO02/32493 discloses formulations which act as carbon dioxide absorbents but contain no Group I metal ions. These formulations contain silica, which increases the porosity of the product and results in good absorption properties without loss of physical stability. These formulations allow a rapid enough reaction between carbon dioxide and calcium hydroxide despite the absence of sodium hydroxide. However, in the absence of sodium hydroxide, the associated catalytic step discussed above cannot take place. Thus the lifetime of such absorbents is sometimes significantly shorter than is desired.

There have now been devised chemical absorbents which overcome or substantially mitigate the above-mentioned and/or other disadvantages of the prior art.

According to a first aspect of the invention, there is provided a chemical absorbent comprising a hydrated mixture of a major proportion of a pharmaceutically acceptable hydroxide of a Group II metal and a minor proportion of a Group I metal-containing zeolite, the chemical absorbent being substantially free of Group I metal hydroxides.

The chemical absorbent according to the invention is advantageous primarily in that it does not react with volatile anaesthetic agents in such a way as to cause the build-up of toxic substances (in particular through the formation of carbon monoxide and the products of exothermic degradation reactions) within an anaesthetic breathing circuit containing anaesthetic agents such as those known as sevoflurane, desflurane, isoflurane, enflurane and halothane. In addition, the absorbent is beneficial in that the Group I metal-containing zeolite acts as a catalyst to accelerate and prolong absorption.

Although alkali metal ion-containing zeolite has been used in absorbents before, it has been necessary for it to be used in conjunction with alkali hydroxide for there to be sufficient absorption capacity and longevity. In the present invention the desired absorption capacity and longevity is achieved without the presence of alkali hydroxide. The absorbent does not require the presence of alkali hydroxides to provide the catalytic reaction step to prolong absorption. Instead the Group I metal-containing zeolite provides a supply of alkali metal ions for the catalytic step.

By the term "substantially free of hydroxides of Group I metals" is meant that the formulation contains a sufficiently low concentration of any such hydroxides for there to be no significant danger of interaction between such hydroxides and any anaesthetic agents with which the chemical absorbent is used. In quantitative terms, "substantially free of hydroxides of Group I metals" may mean that the formulation contains less than 0.5% w/w of such hydroxides, eg less than 0.4%, less than 0.3%, less than 0.2%, or more preferably less than 0.1% w/w.

The pharmaceutically acceptable Group II hydroxide is preferably insoluble or only sparingly soluble in water, and has a high capacity for carbon dioxide absorption. The pharmaceutically acceptable hydroxide may be barium hydroxide or magnesium hydroxide, but is most commonly calcium hydroxide.

The Group II hydroxide may account for 80-99%, or 90-98%, or 92-97%, or 92-96% w/w, or 94-96% w/w of the chemical absorbent of the invention (on a dry basis).

The proportions of the pharmaceutically acceptable hydroxide and the zeolite may vary within quite wide ranges. The Group I metal-containing zeolite may account for 1% to 20% w/w of the mixture (on a dry basis), but more preferably is from 2% to 10% w/w, eg from 3% to 8% w/w, or from 4% to 8% w/w, or from 4% to 6% w/w. The presently preferred percentage of Group I metal-containing zeolite is about 5% w/w (dry weight).

The Group I metal-containing zeolite may account for between 3% and 6% w/w of the chemical absorbent.

The chemical absorbent of the invention may contain 10-25% w/w of water, or from 12-21% w/w, or 14-20% w/w.

Zeolites are microporous crystalline solids with well-defined structures. The framework of zeolites generally comprises silicon, aluminium and oxygen with the aluminium and silicon atoms at the centre of oxygen atom tetrahedra. The well-defined porous structures give rise to a number of applications such as molecular sieving and ion exchange.

The pores of the zeolite structure can contain cations, water and other molecules. The cations may be metal ions and these are generally loosely bound to the zeolite. It is therefore possible to exchange the metal ions with other metal ions in solution. In Group I metal-containing zeolites the Group I metal is thought to be present as Group I metal ions.

Various forms of Group I metal-containing zeolite, eg zeolites containing sodium or potassium, may be utilised. The zeolite is most preferably a sodium-containing zeolite.

Without wishing to be bound by theory, it is believed that the use of the Group I metal-containing zeolite in combination with a pharmaceutically acceptable Group II metal hydroxide and sufficient water allows release of alkali metal ions in exchange for Group II metal ions during the absorption process. These alkali metal ions, in the aqueous state, increase hydroxyl concentration and enable the catalytic reaction step, and so prolong absorption as would be achieved had alkali hydroxide been present.

The zeolite may have increased porosity. This increases the surface contact area, thus increasing the concentration of alkali metal ions available in the system. This in turn increases the efficiency of the chemical absorbent. The increase in porosity may be achieved by adjusting paste water contents and/or using lower temperature drying conditions, during its manufacture.

The chemical absorbent according to the invention preferably consists essentially of a hydroxide of a Group II metal, a Group I metal-containing zeolite and water, other components such as pH-sensitive dye and/or other pigments being present only in trace amounts, typically less than 1% w/w and more preferably less than 0.5% or 0.1% w/w.

According to another aspect of the invention, there is provided a process for the manufacture of a chemical absorbent according to the first aspect of the invention, which comprises the steps of
 a) mixing a pharmaceutically acceptable hydroxide and a Group I metal-containing zeolite;
 b) adding water to form a paste; and
 c) extruding or moulding the paste to form granules.

The process may further comprise drying the granules.

Preferably the granules are spherical and may be formed by passing the paste between a pair of counter-rotating rollers, the rollers having formed therein corresponding hemispherical depressions. Spherical granules are advantageous because they have no projecting edges or corners which can break off and create dust. They are also less friable than conventional granules and maintain the integrity of their shape throughout normal use.

The granules are subsequently dried to the desired water content. In some cases, it may be advantageous to dry the granules to a lower water content (eg complete or substantially complete dryness) and then to rehydrate to the desired final water level. The preferred final water content is 12-21% w/w water content, more commonly 14-20% w/w. This provides sufficient water for absorption reactions to occur. Drying may be carried out at a temperature greater than 125° C., eg 130° C. The drying temperature is preferably no greater than 150° C., eg up to 140° C. or 145° C. In some circumstances, it may be beneficial to carry out an initial drying step at lower temperature, eg 90-100° C., followed by further drying at the temperatures mentioned above.

During the manufacturing process, the zeolite and Group II hydroxide are mixed, and water is added to form a paste with a water content of 30% to 40% w/w, eg 32% to 40% w/w, preferably 33-38% w/w.

In order to provide a visual indication of exhaustion the absorbent according to the invention preferably includes a pH-sensitive dye. Such a dye will generally be present at very low levels, typically 0.001% to 0.1% by weight. The nature of the colour change may, if desired, be modified by incorporation of a pigment in the formulation. For example, trace levels (say around 0.05%) of the pigment sold as EXP GREEN DISP (JKM9/53) by Holliday Dispersions-Kenroy Ltd (Holt Mill Road, Waterfoot, Rossendale, Lancashire BB4 7JB, United Kingdom), which is an aqueous dispersion of CI Pigment Yellow 13 and CI Pigment Green 7, confer on the fresh product a green colour which is replaced by violet upon exhaustion.

The chemical absorbent according to the invention is most preferably used in the form of granules. Such granules may have any suitable shape, but are preferably cylindrical or, most preferably, spherical or substantially spherical (eg biconvex). In other embodiments, the chemical absorbent may be incorporated into components such as filter membranes or formed into monolithic solid blocks.

A specific method by which the chemical absorbent according to the invention may be manufactured is as follows:
 a) Required quantities of the Group II metal hydroxide, zeolite and indicator dye (all in the form of fine powders) are mixed to form a homogeneous powder mix.
 b) Sufficient water is added, with mixing, to form a homogeneous stiff paste. Before the above paste is processed it has been found to be beneficial to allow a dwell time of 20 to 60 minutes, during which the paste hardens to a stiffer consistency.
 c) The paste is then loaded into a processor. The processor comprises two counter-rotating and touching rollers. The direction of rotation of the rollers at the point where they touch is such that the surface of both rollers has a downward motion. Each roller is profiled with hemispherical cavities, each cavity being of the same diameter. Depending on the product to be made, this may be, for example, 3, 3.5 or 4 mm. The hemispherical cavities are arranged in a hexagonal close packed arrangement.
 d) Paste is fed in lumps into a feed hopper mounted on top of the processor. The motion of the rollers draws paste down between them at the point where they touch. Paste is thus squeezed and forced to fill the spherical moulds as they form. As the rollers rotate, the spherical cavities re-open exposing a row of moulded paste spheres. Air knives are mounted adjacent each roller such that a blade of high velocity and energetic air is directed at a tangent to the surface of the rollers down their entire length thus ejecting them from the cavities. A conveyor belt collects the spheres as they drop.

e) The moulded spheres travel along the conveyor and into a continuous belt oven. The first drying stage is a gentle drying at around 100° C. during which the majority of the water is removed from the product. This low temperature stage is believed to prevent rapid drying which could create stress within the structure, reducing the subsequent physical strength of the product. The second drying stage is at an elevated temperature of about 130° C. The final product contains a level of water of about 16%. If initially dried to a lower water content, water may be added back into the product by adding the necessary quantity of water to the dry product which is then mechanically agitated for a sufficient time to disperse the water. The product is then sealed in an airtight container until complete equilibrium of the moisture has taken place.

f) The product may contain partially formed spheres and/or fine particles created during the wetting back process. In order to remove these, the product is sieved over a suitable screen before packing.

Alternatively, other manufacturing processes may be used. For instance, the paste may be extruded through a perforated plate or die to form elongate rods which are dried and then broken down to form granules.

In another aspect of the invention, there is provided a method of removing carbon dioxide from a mixture of gases, the method comprising contacting the mixture of gases with a chemical absorbent according to the first aspect of the invention.

Chemical absorbents of the present invention, and a method for their manufacture, will now be described in greater detail, by way of illustration only, with reference to the following Examples.

Abbreviations
USP=United States Pharmacopoeia
BP=British Pharmacopoeia
FGF=Fresh Gas Flushing General Methods In each Example, a dry mixture of zeolite and calcium hydroxide was prepared in the specified proportions, and water added to give a paste with the specified moisture content. The paste was extruded to form granules, and the granules were dried at the specified drying temperature to the specified end product moisture content.

HCl titration was used to determine the equivalent sodium hydroxide content of the end product.

The end product particle (granule) sizes were determined by USP mesh analysis. In all cases, 90% of the granules had sizes between 2.36 and 4.75 mm.

For each product, the characteristics and performance were assessed in terms of some or all of:

a) Time taken for breakthrough of $CO_2$ to reach 0.2% determined by BP method: The activity is not less than 120 minutes when determined by the following method. Use a vertically-clamped tube of glass or other suitable transparent material about 25 cm long and 29 to 31 mm internal diameter with closely fitting rubber bungs at each end; the bungs are bored to receive polythene or glass tubing being flush with the inner ends of the bungs. With the lower bung in position, place sufficient nylon mesh support on top of the bung to produce a bed of mesh about 10 cm deep and press a closely fitting disc of stainless steel gauze of nominal mesh aperture about 500 μm on top of the nylon mesh so that its surface is at right angles to the axis of the tube. Introduce 59.8 to 60.2 g pf the substance being examined onto the steel gauze in three portions, tamping lightly after the addition of each portion. Place a second disc of steel gauze on top, followed by a sufficient quantity of nylon mesh such that the soda lime is kept consolidated by slight pressure when the second bung has been inserted. The exit tube is connected to a condenser, consisting of two 50 mL separating funnels, leading to a drying tube packed with anhydrous calcium chloride and then to a carbon dioxide analyser sufficiently sensitive to detect 0.2% v/v of carbon dioxide. A katharometer, calibrated for carbon dioxide and preferably used in conjunction with a chart recorder, is suitable. Using the gas analyser in accordance with the manufacturer's instructions, accurately determine the carbon dioxide content, p, as a percentage v/v of a nominal 5% carbon dioxide mixture, the balance gas being oxygen, air or nitrogen as appropriate to the type of gas analyser being used. Suitable compressed gas mixtures are available commercially. Assemble the apparatus described above and pass the gas mixture downwards into the absorption tube at a rate of 900 cm³ per minute until such time that the gas analyser shows the content of carbon dioxide in the effluent gas to have risen to 0.2% v/v. Steps should be taken to vent the effluent gas if an oxygen-carbon dioxide mixture is being used. Record the time taken, t, in minutes. The activity of the substance being examined is given, in minutes, by the expression tp/5. A similar method is used to assess the time taken for breakthrough of $CO_2$ to reach 0.01%.

b) Maximum level of CO generation when dry (630 ml dry absorbent, 0.5% water content, 2 L/min $O_2$ containing 5% isoflurane) determined by the following method: The dried absorbents (630 ml) are contained within an absorber and subjected to a 2 L/min flow of dry oxygen (20° C. to 23° C.) containing 5% isoflurane as vapour. The gas emerging from the absorbent is analysed for carbon monoxide using a 7000 series ADC infra-red carbon monoxide monitor. The test rig is assembled as an open system (no recycling). This enables direct measurement of breakdown products emerging from the absorbent rather than an accumulative build up.

c) Bulk density determined by the following method: Weigh an empty 500 ml cylinder and note the weight (W1) in grams. Fill the cylinder with the substance being examined in three equal increments, tamping between each addition so as to settle the sample. Continue adding and tamping until the volume reaches the 500 ml mark. Weigh the full measuring cylinder and note the weight (W2) in grams. The tamped bulk density=((W2−W1)/500)×1000 in g/litre.

d) Moisture content after FGF for 8 hours: determined by USP method, FGF consisting of upward flow of dry air (15 L/min flow of air passed through a 1 L bed of molecular sieve to bring it to 0% relative humidity) through 100 g of absorbent (a shallow bed of 80 mm diameter).

The relative humidity of the outlet gas from the absorbent is continually measured.

Example 1

5% w/w sodium zeolite (dry basis)
95% w/w calcium hydroxide (dry basis)
36% w/w paste moisture
Drying temperature: 130° C.
HCl titration: 0.9%
End product moisture: 16%
Particle shape: short 2.7 mm diameter strands
$CO_2$ breakthrough: 145 mins to 0.01% $CO_2$, 171 mins to 0.2% $CO_2$
Max CO generation when dry: 54 ppm
Moisture content after FGF drying: 2.1% w/w Example 2

5% w/w sodium zeolite (dry basis)
95% w/w calcium hydroxide (dry basis)

36% w/w paste moisture
Drying temperature: 140° C.
HCl titration: 0.9%
End product moisture: 16%
Particle shape: short 2.7 mm diameter strands
$CO_2$ breakthrough: 121 mins to 0.01% $CO_2$, 144 mins to 0.2% $CO_2$
Max CO generation when dry: 45 ppm
Moisture content after FGF drying: 2.3% w/w Example 3

5% w/w sodium zeolite (dry basis)
95% w/w calcium hydroxide (dry basis)
36% w/w paste moisture
Drying temperature: 150° C.
HCl sodium hydroxide equivalent titration: 0.9%
End product moisture: 16%
Particle shape: short 2.7 mm diameter strands
$CO_2$ breakthrough: 87 mins to 0.01% $CO_2$, 129 mins to 0.2% $CO_2$
Max CO generation when dry: 41 ppm
Moisture content after FGF drying: 2.3% w/w Example 4

5% w/w sodium zeolite (dry basis)
95% w/w calcium hydroxide (dry basis)
35% w/w paste moisture
Drying temperature: 130° C.
HCl sodium hydroxide equivalent titration: 0.9%
End product moisture: 16%
Particle shape: short 2.7 mm diameter strands
$CO_2$ breakthrough: 135 mins to 0.01% $CO_2$, 157 mins to 0.2% $CO_2$
Moisture content after FGF drying: 2.2% w/w Example 5

5% w/w sodium zeolite (dry basis)
95% w/w calcium hydroxide (dry basis)
34% w/w paste moisture
Drying temperature: 130° C.
HCl sodium hydroxide equivalent titration: 0.9%
End product moisture: 16%
Particle shape: short 2.7 mm diameter strands
$CO_2$ breakthrough: 120 mins to 0.01% $CO_2$, 143 mins to 0.2% $CO_2$
Moisture content after FGF drying: 2.3% w/w Example 6

5% w/w sodium zeolite (dry basis)
95% w/w calcium hydroxide (dry basis)
33% w/w paste moisture
Drying temperature: 130° C.
HCl sodium hydroxide equivalent titration: 0.9%
End product moisture: 16%
Particle shape: short 2.7 mm diameter strands
$CO_2$ breakthrough: 105 mins to 0.01% $CO_2$, 126 mins to 0.2% $CO_2$
Moisture content after FGF drying: 2.5% w/w Example 7

5% w/w sodium zeolite (dry basis)
95% w/w calcium hydroxide (dry basis)
30% w/w paste moisture
Drying temperature: 130° C.
HCl sodium hydroxide equivalent titration: 0.9%
End product moisture: 16%
Particle shape: short 2.7 mm diameter strands
$CO_2$ breakthrough: 13 mins to 0.01% $CO_2$, 26 mins to 0.2% $CO_2$
Moisture content after FGF drying: 2.5% w/w Example 8

5% w/w sodium zeolite (dry basis)
95% w/w calcium hydroxide (dry basis)
40% w/w paste moisture
Drying temperature: 130° C. End product moisture: 16%
Particle shape: short 2.7 mm diameter strands
$CO_2$ breakthrough: 137 mins to 0.01% $CO_2$, 158 mins to 0.2% $CO_2$
Moisture content after FGF drying: 1.9% w/w Example 9

2% w/w sodium zeolite (dry basis)
98% w/w calcium hydroxide (dry basis)
36% w/w paste moisture
Drying temperature: 130° C.
HCl sodium hydroxide equivalent titration: 0.4%
End product moisture: 16%
Particle shape: short 2.7 mm diameter strands
$CO_2$ breakthrough: 130 mins to 0.01% $CO_2$, 156 mins to 0.2% $CO_2$
Max CO generation when dry: 22 ppm
Bulk density: 0.68 kg/L
Moisture content after FGF drying: 1.5% w/w Example 10

1% w/w sodium zeolite (dry basis)
99% w/w calcium hydroxide (dry basis)
36% w/w paste moisture
Drying temperature: 130° C.
HCl sodium hydroxide equivalent titration: 0.1%
End product moisture: 16%
Particle shape: short 2.7 mm diameter strands
$CO_2$ breakthrough: 87 mins to 0.01% $CO_2$, 124 mins to 0.2% $CO_2$
Moisture content after FGF drying: 1.3% w/w Example 11

7.5% w/w sodium zeolite (dry basis)
92.5% w/w calcium hydroxide (dry basis)
36% w/w paste moisture
Drying temperature: 130° C.
HCl sodium hydroxide equivalent titration: 1.3%
End product moisture: 16%
Particle shape: short 2.7 mm diameter strands
$CO_2$ breakthrough: 134 mins to 0.01% $CO_2$, 153 mins to 0.2% $CO_2$
Max CO generation when dry: 83 ppm
Bulk density: 0.78 kg/L
Moisture content after FGF drying: 3.3% w/w Example 12

10% w/w sodium zeolite (dry basis)
90% w/w calcium hydroxide (dry basis)
36% w/w paste moisture
Drying temperature: 130° C.
HCl sodium hydroxide equivalent titration: 2.1%
End product moisture: 16%
Particle shape: short 2.7 mm diameter strands $CO_2$ breakthrough: 119 mins to 0.01% $CO_2$, 133 mins to 0.5% $CO_2$
Max CO generation when dry: 115 ppm
Bulk density: 0.79 kg/L
Moisture content after FGF drying: 3.9% w/w Example 13

15% w/w sodium zeolite (dry basis)
85% w/w calcium hydroxide (dry basis)
36% w/w paste moisture
Drying temperature: 130° C.
HCl sodium hydroxide equivalent titration: 2.9%
End product moisture: 16%
Particle shape: short 2.7 mm diameter strands
$CO_2$ breakthrough: 109 mins to 0.01% $CO_2$, 118 mins to 0.2% $CO_2$
Moisture content after FGF drying: 5.5% w/w Example 14

20% w/w sodium zeolite (dry basis)
80% w/w calcium hydroxide (dry basis)
36% w/w paste moisture
Drying temperature: 130° C.
HCl sodium hydroxide equivalent titration: 4.2%
End product moisture: 16%
Particle shape: short 2.7 mm diameter strands
$CO_2$ breakthrough: 74 mins to 0.01% $CO_2$, 118 mins to 0.2% $CO_2$
Moisture content after FGF drying: 3.3% w/w Example 15

5% w/w sodium zeolite (dry basis)
95% w/w calcium hydroxide (dry basis)
36% w/w paste moisture
Drying temperature: 130° C.
HCl sodium hydroxide equivalent titration: 0.9%
End product moisture: 5%
Particle shape: short 2.7 mm diameter strands
$CO_2$ breakthrough: 5 mins to 0.01% $CO_2$, 21 mins to 0.2% $CO_2$
Moisture content after FGF drying: 2.1% w/w Example 16

5% w/w sodium zeolite (dry basis)
95% w/w calcium hydroxide (dry basis)
36% w/w paste moisture
Drying temperature: 130° C.
HCl sodium hydroxide equivalent titration: 0.9%
End product moisture: 10%
Particle shape: short 2.7 mm diameter strands
$CO_2$ breakthrough: 125 mins to 0.01% $CO_2$, 142 mins to 0.2% $CO_2$
Moisture content after FGF drying: 2.1% w/w

REFERENCE EXAMPLES

The following Reference Examples do not fall within the scope of the invention and are provided for comparison purposes.

Reference Example 1 (No Zeolite, No Alkali Metal Hydroxide)

100% w/w calcium hydroxide (dry basis)
35% w/w paste moisture
Drying temperature: 130° C.
HCl titration: 0.0%
End product moisture: 16%
Particle shape: short 2.7 mm diameter strands
$CO_2$ breakthrough: 86 mins to 0.01% $CO_2$, 105 mins to 0.2% $CO_2$
Moisture content after FGF drying: 0.9% w/w Reference Example 2 (No Zeolite, 3% Sodium Hydroxide)

97% w/w calcium hydroxide (dry basis)
3% w/w sodium hydroxide (dry basis)
35% w/w paste moisture
Drying temperature: 130° C.
HCl titration: 3.0%
End product moisture: 16%
Particle shape: short 2.7 mm diameter strands
$CO_2$ breakthrough: 139 mins to 0.01% $CO_2$, 163 mins to 0.2% $CO_2$
Max CO generation when dry: 385 ppm
Moisture content after FGF drying: 1.1% w/w Discussion a) Effect of Drying Temperature Examples 1, 2 and 3 show the effect of varying the drying temperature on the performance of the chemical absorbent. Lower drying temperatures are shown to increase the $CO_2$ capacity of the absorbent. The desiccation by FGF drying for 8 hours is acceptable at each of the drying temperatures. These results are summarised in Table 1:

TABLE 1

| Example No | Drying temperature/ ° C. | Residual moisture after FGF drying (% w/w) | Time to 0.2% $CO_2$ breakthrough (minutes) |
| --- | --- | --- | --- |
| 1 | 130 | 2.1 | 171 |
| 2 | 140 | 2.3 | 144 |
| 3 | 150 | 2.3 | 129 | b) Effect of Paste Moisture Content

Examples 1 and 4 to 8 show the effect of varying the paste moisture content on the performance of the chemical absorbent. 36% paste moisture content is shown to provide the greatest $CO_2$ capacity. The desiccation by FGF drying for 8 hours is acceptable for each of the values of paste moisture content but is shown to increase with increasing paste moisture content. These results are summarised in Table 2:

TABLE 2

| Example No | Paste moisture content (% w/w) | Residual moisture after FGF drying (% w/w) | Time to 0.2% $CO_2$ breakthrough (minutes) |
| --- | --- | --- | --- |
| 8 | 40 | 1.9 | 158 |
| 1 | 36 | 2.1 | 171 |
| 4 | 35 | 2.2 | 157 |
| 5 | 34 | 2.3 | 143 |
| 6 | 33 | 2.5 | 126 |
| 7 | 30 | 2.5 | 26 | c) Effect of Sodium Zeolite Concentration

Examples 1 and 9 to 14 show the effect of varying the sodium zeolite concentration on the performance of the chemical absorbent. 5% sodium zeolite concentration is shown to most increase the $CO_2$ capacity of the absorbent. The desiccation by FGF drying for 8 hours is acceptable for all values above 2% w/w sodium zeolite concentration, though increased sodium zeolite concentration does increase CO production when dry. These results are summarised in Table 3:

TABLE 3

| Example No | Sodium zeolite concentration (dry % w/w) | Residual moisture after FGF drying (% w/w) | Time to 0.2% $CO_2$ breakthrough (minutes) | Maximum CO generation when dry (ppm) |
| --- | --- | --- | --- | --- |
| 10 | 1 | 1.3 | 124 | |
| 9 | 2 | 1.5 | 156 | 22 |
| 1 | 5 | 2.1 | 171 | 54 |
| 11 | 7.5 | 3.3 | 153 | 83 |
| 12 | 10 | 3.9 | 133 | 115 |
| 13 | 15 | 5.5 | 118 | |
| 14 | 20 | 3.3 | 118 | | d) Effect of End Product Moisture Content

Examples 1, 15 and 16 show the effect of varying the end product moisture content on the performance of the chemical absorbent (other manufacturing parameters being identical). Altering the end product moisture content does not change the degree of desiccation by FGF drying for 8 hours. However, insufficient moisture in the end product is shown to significantly reduce $CO_2$ capacity. These results are summarised in Table 4

TABLE 3

| Example No | End product moisture content (% w/w) | Residual moisture after FGF drying (% w/w) | Time to 0.2% $CO_2$ breakthrough (minutes) |
| --- | --- | --- | --- |
| 15 | 5 | 2.1 | 21 |
| 16 | 10 | 2.1 | 142 |
| 1 | 16 | 2.1 | 171 | e) Reference Examples

Reference Examples 1 and 2 are control experiments and show that increased desiccation by FGF drying for 8 hours is observed in the absence of sodium zeolite and also in the absence of sodium zeolite and the presence of 3% sodium hydroxide. Reference Example 1 also shows that insufficient $CO_2$ capacity is achieved in the absence of sodium, either from sodium zeolite or sodium hydroxide.

The invention claimed is:

1. A chemical absorbent consisting of:
   a hydrated mixture of a major proportion of a pharmaceutically acceptable hydroxide of a Group II metal and a minor proportion of a Group I metal-containing zeolite, and one or more pH-sensitive dyes and/or other pigments;
   wherein
   the pharmaceutically acceptable hydroxide of a Group II metal is present in an amount of between 92% and 97% w/w of the chemical absorbent (on a dry basis);
   the Group I metal-containing zeolite is present in an amount of between 3% and 8% w/w of the chemical absorbent (on a dry basis);
   the dyes and/or pigments are present in an amount of less than 0.5% w/w of the chemical absorbent (on a dry basis);
   the chemical absorbent contains less than 0.5% w/w (on a dry basis) of hydroxides of Group I metals; and
   the chemical absorbent has a water content of between 12% and 21% w/w.

2. A chemical absorbent comprising a hydrated mixture of a major proportion of a pharmaceutically acceptable hydroxide of a Group II metal and a minor proportion of a Group I metal-containing zeolite, the chemical absorbent comprising less than 0.5% w/w of hydroxides of Group I metals, other components being present only in amounts of less than 1% w/w (on a dry basis).

3. A chemical absorbent as claimed in claim 2, wherein the pharmaceutically acceptable hydroxide is calcium hydroxide.

4. A chemical absorbent as claimed in claim 2, wherein the pharmaceutically acceptable hydroxide accounts for 80-99% w/w (on a dry basis) of the chemical absorbent.

5. A chemical absorbent as claimed in claim 2, wherein the Group I metal containing zeolite accounts for 1-20% w/w (on a dry basis) of the chemical absorbent.

6. A chemical absorbent as claimed in claim 2, wherein the Group I metal-containing zeolite accounts for between 3% and 6% w/w of the chemical absorbent.

7. A chemical absorbent as claimed in claim 2, which contains between 14% and 20% w/w of water.

8. A chemical absorbent as claimed in claim 2, which consists essentially of the hydroxide of a Group II metal, Group I metal-containing zeolite and water, other components being present only in amounts of less than 1% w/w (on a dry basis).

9. A chemical absorbent as claimed in claim 2, which consists solely of the hydroxide of a Group II metal, Group I metal-containing zeolite, water, and one or more pH-sensitive dyes and/or other pigments, the dyes and/or pigments accounting for less than 1% w/w of the composition (on a dry basis).

10. A chemical absorbent as claimed in claim 2, wherein the Group I metal-containing zeolite is a sodium-containing zeolite.

11. A chemical absorbent as claimed in claim 2, which further comprises a pH-sensitive dye.

12. A chemical absorbent as claimed in claim 11, wherein the pH-sensitive dye is present at a level of 0.001% to 0.1% by weight (on a dry basis).

13. A chemical absorbent as claimed in claim 2, which further comprises a pigment.

14. A chemical absorbent as claimed in claim 2, which is in the form of granules.

15. A chemical absorbent as claimed in claim 14, wherein the granules are cylindrical, spherical or substantially spherical.

16. A method of removing carbon dioxide from a mixture of gases, the method comprising contacting the mixture of gases with a chemical absorbent as claimed in claim 2.

* * * * *